US008956311B2

(12) United States Patent
Korb et al.

(10) Patent No.: US 8,956,311 B2
(45) Date of Patent: Feb. 17, 2015

(54) METHODS FOR DIAGNOSING MEIBOMIAN GLAND DYSFUNCTION

(75) Inventors: Donald R. Korb, Boston, MA (US); Caroline Blackie, North Andover, MA (US); Christy Stevens, Cary, NC (US)

(73) Assignee: TearSciecne, Inc., Morrisville, NC (US)

( * ) Notice: Subject to any disclaimer, the term of this patent is extended or adjusted under 35 U.S.C. 154(b) by 512 days.

(21) Appl. No.: 13/271,768

(22) Filed: Oct. 12, 2011

(65) Prior Publication Data

US 2012/0265101 A1    Oct. 18, 2012

Related U.S. Application Data

(60) Provisional application No. 61/392,777, filed on Oct. 13, 2010.

(51) Int. Cl.
*A61B 5/103* (2006.01)
*A61B 5/00* (2006.01)
*A61B 3/10* (2006.01)

(52) U.S. Cl.
CPC ............... *A61B 5/4261* (2013.01); *A61B 3/10* (2013.01)
USPC ............................ 600/587; 604/289; 351/206

(58) Field of Classification Search
CPC ......... A61B 3/10; A61B 3/101; A61B 5/4261
USPC ............................ 600/587; 604/289; 351/206
See application file for complete search history.

(56) References Cited

U.S. PATENT DOCUMENTS

| 3,411,364 A | 11/1968 | Horley et al. |
| 4,951,671 A | 8/1990 | Coan |
| 5,224,469 A | 7/1993 | Mocny |
| 5,830,139 A | 11/1998 | Abreu |
| 7,025,763 B2 | 4/2006 | Karasawa et al. |
| 7,654,669 B2 | 2/2010 | Suzuki |

(Continued)

FOREIGN PATENT DOCUMENTS

| WO | 2012137545 A1 | 10/2012 |
| WO | 2013114127 A1 | 8/2013 |
| WO | 2013166353 A1 | 11/2013 |

OTHER PUBLICATIONS

Korb et al. "Miebomian Gland Diagnostic Expressibility: Correlation with Dry Eye Sympltoms and Gland Location." Cornea, vol. 27, Dec. 2008, pp. 1142-1147. (submitted by applicant.*

(Continued)

*Primary Examiner* — Max Hindenburg
*Assistant Examiner* — Renee Danega
(74) *Attorney, Agent, or Firm* — Withrow & Terranova PLLC

(57) ABSTRACT

Methods of diagnosing meibomian gland dysfunction are disclosed. The methods may be standardized and provide an accurate diagnosis of whether meibomian gland dysfunction exists. In one embodiment, a method is provided that utilizes an evaluation tool to apply a force for a preselected period of time to at least one of a plurality of meibomian glands in two or more regions of a plurality of regions of an eyelid. A grade is assigned to the at least one meibomian gland of the plurality of meibomian glands in each of the two or more regions based on any secretion that is expressed from each meibomian gland. In this manner, a plurality of meibomian gland secretion grades is obtained. The plurality of meibomian gland secretion grades is indicative of the presence of meibomian gland dysfunction.

20 Claims, 11 Drawing Sheets

(56) References Cited

U.S. PATENT DOCUMENTS

2008/0082057 A1* 4/2008 Korb et al. .................. 604/289
2010/0100029 A1 4/2010 Maskin

OTHER PUBLICATIONS

McGinnigle, S. et al., "Evaluation of Dry Eye," Survey of Ophthalmology, vol. 57, Iss. 4, Jul./Aug. 2012, pp. 293-316.
Wladis, E. "Intraductal meibomian gland probing in the management of ocular rosacea," Ophthalmic Plastic and Reconstructive Surgery, vol. 28, No. 6, Oct. 2012, pp. 416-418.
International Preliminary Report on Patentability for PCT/US2011/055971 mailed Apr. 25, 2013, 6 pages.
Korb, Donald R., O.D. et al., "Meibomian Gland Dysfunction and Contact Lens Intolerance," Jnl American Optometric Association, vol. 51, No. 3, Mar. 1980, pp. 243-251.
Korb, Donald R. et al., "Increase in Tear Film Lipid Layer Thickness Following Treatment of Meibomian Gland Dysfunction," Lacrimal Gland, Tear Film and Dry Eye Syndromes: Basic Science Clinical Relevance, Adv. Exp. Med. Biol., vol. 350, 1994, pp. 293-298.
Maskin, Steven L., M.D., "Intraductal Meibomian Gland Probing Relieves Symptoms of Obstructive Meibomian Gland Dysfunction," AVRO Poster # 4636, 1 page.
Korb, Donald R. et al., "Lid Wiper Epitheliopathy and Dry Eye Symptoms," Eye & Contact Lens, vol. 31, No. 1, 2005, pp. 2-8.
Foulks, G.N., "The Correlation Between the Tear Film Lipid Layer and Dry Eye Disease," Survey of Ophthalmology, vol. 52, No. 4, Jul.-Aug. 2007, pp. 369-374.
Blackie, Caroline A. et al., "The Diurnal Secretory Characteristics of Individual Meibomian Glands," Cornea, vol. 29, No. 1, Jan. 2010, pp. 34-38.
Korb, Donald R. et al., "Meibomian Gland Diagnostic Expressibility: Correlation with Dry Eye Symptoms and Gland Location," Cornea, vol. 27, No. 10, Dec. 2008, pp. 1142-1147.
Norn, M.S., "Expressibility of Meibomian Secretion: Relation to Age, Lipid Precorneal Film, Scales, Foam, Hair and Pigmentation," Acta Ophthalmologica, vol. 65, 1987, pp. 137-142.
Lemp, Michael et al., "Tear osmolarity in the diagnosis and management of dry eye disease," American Journal of Ophthalmology, vol. 151, No. 5, May 2011, pp. 792-798.
Blackie, C. et al., "Recovery Time of an Optimally Secreting Meibomian Gland," Cornea, vol. 28, No. 3, Apr. 2009, pp. 293-297.
Kolis, "Randomized Clinical Trial for Treatment of Meibomian Gland Dysfunction and Evaporative Dry Eye," LF-001 Revision A, Dec. 22, 2008, 70 pages.
Blackie, C. et al., "Non-obvious Obstructive Meibomian Gland Dysfunction," Paper in press, Jan. 11, 2009, 40 pages.
Stevens, C., "LF-001: Final Clinical Study Report," Nov. 2009, 130 pages.
Arita, Reiko et al., "Objective image analysis of the meibomian gland area," British Journal of Ophthalmology, vol. 98, No. 6, 2014, BMJ Publishing Group, pp. 746-755.

* cited by examiner

| MEIBOMIAN GLAND SECRETION GRADING SCALE ||
|---|---|
| GRADE | SECRETION CHARACTERISTICS |
| 3 | CLEAR LIQUID OIL |
| 2 | COLORED/CLOUDY LIQUID |
| 1 | INSPISSATED (TOOTHPASTE-CONSISTENCY) |
| 0 | NO SECRETION (INCLUDES CAPPED ORIFICES) |

*FIG. 6*

METHODS FOR DIAGNOSING MEIBOMIAN GLAND DYSFUNCTION

RELATED APPLICATIONS

The present application claims priority to U.S. Provisional Patent Application No. 61/392,777 entitled "Methods for Diagnosing Meibomian Gland Dysfunction," filed on Oct. 13, 2010, which is incorporated herein by reference in its entirety.

The present application is also related to U.S. application Ser. No. 11/541,240 filed on Sep. 29, 2006, and entitled "Methods and Apparatus for Diagnosing Meibomian Gland Dysfunction," which is incorporated herein by reference in its entirety.

The present application is being filed with a color version of FIG. 7 discussed and referenced in this disclosure. The color drawing more fully discloses the subject matter disclosed herein.

FIELD OF THE DISCLOSURE

The field of disclosure is ophthalmology and more particularly diagnosing and treating dry eye disease as it relates to the health of the meibomian glands. More particularly, the present application relates to diagnosis and treatment of meibomian gland dysfunction (MGD), which may be either responsible for or a contributing factor to a patient suffering from a "dry eye" condition.

BACKGROUND

The human body contains a number of glands including the lacrimal and meibomian glands of the eye, the sebaceous or pilo-sebaceous hair glands on the face and underarms, and the mammary glands in the breasts. These glands may malfunction due to age, irritation, environmental conditions, cellular debris, inflammation, hormonal imbalance and other causes. One common disease state of the eyelid glands is the restriction or stoppage of the natural flow of fluid out of the gland caused by an obstruction.

In the human eye, the tear film covering the ocular surfaces is composed of three layers. The innermost layer in contact with the ocular surface is the mucus layer comprised of many mucins. The middle layer comprising the bulk of the tear film is the aqueous layer, and the outermost layer is a thin (less than 250 nanometers (nm)) layer comprised of many lipids known as "meibum" or "sebum." The sebum is secreted by the meibomian glands, which are enlarged specialized sebaceous-type glands (hence, the use of "sebum" to describe the secretion) located on both the upper and lower eyelids, with orifices designed to discharge the lipid secretions onto the eyelid margins, thus forming the lipid layer of the tear film. The typical upper eyelid has about twenty-five (25) meibomian glands and the lower eyelid has about twenty (20) meibomian glands, which are somewhat larger than those located in the upper eyelid and which therefore contribute a greater amount of these lipid secretions. The meibomian gland comprises various sac-like acini which discharge the secretion into the main central duct of the gland. The secretion then passes into the orifices which are surrounded by smooth muscle tissue and the muscle of Riolan which are presumed to aid in the expression of sebum. The meibomian gland orifices open onto the eyelid margin at and around the junction of the inner mucous membrane and the outer skin of the eyelids' mucocutaneous junction.

Specifically, each meibomian gland has a straight long central duct lined with four (4) epithelial layers on the inner surface of the duct. Along the length of the central duct there are multiple lateral out-pouching structures, termed acini, where the secretion of the gland is manufactured. The inner lining of each acinus differs from the main central duct in that these specialized cells provide the secretions of the meibomian gland. The secretions flow from each acinus to the duct. There appears to be a valve system between each acinus and the central duct to retain the secretion until it is required, at which time it is discharged into the central duct. The meibomian secretion is then stored in the central duct and is released through the orifice of each gland onto the eyelid margin. Blinking and the squeezing action of the muscle of Riolan surrounding the meibomian glands are thought to be the primary mechanisms to open the orifice for the release of secretion from the meibomian gland.

The sebum that forms the outermost lipid layer is secreted by meibomian glands 10 of the eye, as illustrated in FIGS. 1-3. The meibomian glands are enlarged, specialized sebaceous-type glands (hence, the use of "sebum" to describe the secretion) located on both an upper eyelid 12 and a lower eyelid 14. The meibomian glands 10 contain orifices 16 that are designed to discharge lipid secretions onto the eyelid margins, thus forming the lipid layer of the tear film as the mammal blinks and spreads the lipid secretion. The typical human upper eyelid 12 has about twenty five (25) meibomian glands and the lower eyelid 14 has about twenty (20) meibomian glands, which are somewhat larger than those located in the upper eyelid. Each meibomian gland 10 has a straight long channel or central duct 18 lined with four (4) epithelial layers on the inner surface of the central duct 18. The central duct 18 may also be referred to herein as "meibomian gland channel." Along the length of the central duct 18 are multiple lateral out-pouching structures 20, termed acini, where the secretion of the meibomian gland 10 is manufactured. The inner lining of each acinus 20 differs from the main central duct 18 in that these specialized cells provide the secretions of the meibomian gland 10. The secretions flow from each acinus 20 to the central duct 18.

There appears to be a valve system between each acinus 20 and the central duct 18 to retain the secretion until it is required, at which time it is discharged into the central duct 18. The meibomian secretion is then stored in the central duct 18 and is released through the orifice 16 of each meibomian gland 10 onto the eyelid margin. Blinking and the squeezing action of the muscle of Riolan surrounding the meibomian glands 10 are thought to be the primary mechanism to open the orifice 16 for the release of secretion from the meibomian gland 10. Blinking causes the upper eyelid 12 to pull a sheet of the lipids secreted by the meibomian glands 10 over the other two (2) layers of the tear film, thus forming a type of protective coating which limits the rate at which the underlying layers evaporate. Thus, a defective lipid layer or an insufficient quantity of such lipids can result in accelerated evaporation of the aqueous layer which, in turn, causes symptoms such as itchiness, burning, irritation, and dryness, which are collectively referred to as "dry eye."

Dry eye states have many etiologies. A common cause of common dry eye states is the condition known as "meibomian gland dysfunction" (MGD), a disorder where the meibomian glands are obstructed or occluded. As employed herein the terms "occluded" and "obstruction" as they relate to meibomian gland dysfunction are defined as partially or completely blocked or plugged meibomian glands, or any component thereof, including a channel or duct, having a solid, semi-solid or thickened congealed secretion and/or plug, leading to a compromise, or more specifically, a decrease or cessation of secretion. Also, with a reduced or limited secretion, the meibomian gland may be compromised by the occluded or obstructive condition as may be evidenced by a yellowish color indicating a possible infection state, or may be otherwise compromised so that the resulting protective lipid protective film is not adequate.

Meibomitis, an inflammation of the meibomian glands leading to their dysfunction, is usually accompanied by blepharitis (inflammation of the eyelids). Meibomian gland dysfunction may accompany meibomitis, or meibomian gland dysfunction may be present without obvious eyelid inflammation. Meibomian gland dysfunction is frequently the result of keratotic obstructions which partially or completely block the meibomian gland orifices and/or the central duct (canal) of the meibomian gland, or possibly the acini or acini valves (assuming they do in fact exist) or the acini's junction with the central duct. Such obstructions compromise the secretory functions of the individual meibomian glands. More particularly, these keratotic obstructions are comprised of bacteria, sebaceous ground substance, or dead and/or desquamated epithelial cells. See Korb et al., "Meibomian Gland Dysfunction and Contact Lens Intolerance," Journal of the Optometric Association, Vol. 51, Number 3, (1980), pp. 243-251. While meibomitis is obvious by inspection of the external eyelids, meibomian gland dysfunction may not be obvious even when examined with the magnification of a slit-lamp biomicroscope, since there may not be external signs or the external signs may be so minimal that they are overlooked. The external signs of obstructive meibomian gland dysfunction may be limited to subtle alterations of the epithelium of the eyelid margins over the orifices, and pouting of the orifices of the meibomian glands with congealed material acting as obstructions. The external signs of obstructive meibomian gland dysfunction in severe to very severe instances may be obvious, and include serration and distortion of the shape of the eyelid margins. While inflammation is not usually present with mild to moderate obstructive meibomian gland dysfunction, with severe to very severe instances of obstructive meibomian gland dysfunction, inflammation may be present.

There is a correlation between the tear film lipid layer and dry eye disease. The various different medical conditions and damage to the eye and the relationship of the lipid layer to those conditions are reviewed in Sury Opthalmol 52:369-374, 2007. It is clear that the lipid layer condition has the greatest effect on dry eye disease when compared to the aqueous layer or other causes. Thus, while dry eye states have many etiologies, the inability of the meibomian gland 10 to sufficiently generate the lipid layer is a common cause of common dry eye state or MGD. MGD is a disorder where the meibomian glands 10 are obstructed or occluded. FIG. 3 illustrates an example of such obstructions or occlusions 22, 24. Plug obstructions 22 can occur in the orifice 16 of the central duct 18. Alternatively, obstructions and occlusions 22, 24 can occur that block a particular acinus 20. The obstructions or occlusions 22, 24 can mean that the meibomian glands 10 are partially blocked or plugged, completely blocked or plugged, or any variation thereof. Obstructions and occlusions 22, 24 can be in a solid, semi-solid, or thickened, congealed secretion and/or a plug, leading to a compromise, or more specifically, a decrease in or cessation of secretion. It may be appreciated from FIG. 3 that the meibomian glands 10 have a certain amount of depth. The obstructions and occlusions 22, 24 may be located at any depth below the orifice 16 of the meibomian gland 10, and may be located in the central duct 18, in one or more of the acini 20, or at a junction of the central duct 18 and the an acinus 20. Also, with a reduced or limited secretion, the meibomian gland 10 may be compromised by the occluded or obstructive condition often evidenced by a yellowish color, indicating a possible infection state. Alternatively, the meibomian gland 10 may be otherwise compromised so that the resulting protective lipid film is not adequate for preventing evaporation of the underlying layers on the eye.

MGD is frequently the result of keratotic obstructions, which partially or completely block the meibomian gland orifices 16 and/or the central duct (canal) 18 of the meibomian gland 10, or possibly the acini or acini valves (assuming they do in fact exist) or the junction of the acini 20 with the central duct 18. Such obstructions 22, 24 compromise the secretory functions of the individual meibomian glands 10. More particularly, these keratotic obstructions may be associated with or result in various combinations of bacteria, sebaceous ground substance, dead, and/or desquamated epithelial cells (see Korb et al., "Meibomian Gland Dysfunction and Contact Lens Intolerance," Journal of the Optometric Association, Vol. 51, No. 3, (1980), pp. 243-251).

Hormonal changes, which occur during menopause and particularly changing estrogen levels, can result in thickening of the oils secreted by the meibomian glands 10. This may result in clogged meibomian gland orifices. Further, decreased estrogen levels may also enhance conditions under which staphylococcal bacteria can proliferate. This can cause migration of the bacteria into the meibomian glands 10 compromising glandular function and further contributing to occlusion, thus resulting in a decreased secretion rate of the meibomian gland 10.

When the flow of secretions from the meibomian gland 10 is restricted due to the existence of an occlusion 22, 24, cells on the eyelid margin have been observed to grow over the orifice 16. This may further restrict sebum flow and exacerbate a dry eye condition. Additional factors may also cause or exacerbate meibomian gland dysfunction including age, disorders of blinking, activities such as computer use which compromise normal blinking, contact lens use, contact lens hygiene, cosmetic use, or illness, particularly diabetes. It has been theorized that the acini 20 of the meibomian glands 10 may have valves at their junction with the main channel of the meibomian gland 10. It is theorized that if these valves exist, they may also become obstructed in some instances leading to reduced or blocked flow from the acini 20. These obstructions or occlusions 22, 24 may have various compositions.

The state of an individual meibomian gland 10 can vary from optimal, where clear meibomian fluid is produced; to mild or moderate meibomian gland dysfunction where milky fluid or inspissated or creamy secretion is produced; to total blockage, where no secretion of any sort can be obtained (see Korb et al., "Increase in Tear Film Lipid Layer Thickness Following Treatment of Meibomian Gland Dysfunction," Lacrimal Gland, Tear Film, and Dry Eye Syndromes," pp. 293-298, edited by D. A. Sullivan, Plenum Press, New York (1994)). Significant chemical changes of the secretions of the meibomian gland 10 occur with meibomian gland dysfunction and consequently, the composition of the naturally occurring tear film is altered, which in turn contributes to dry eye.

While the tear film operates as a singular entity and all of the layers thereof are important, the lipid layer, which is secreted from the meibomian glands, is of particular significance as it functions to slow the evaporation of the underlying layers and to lubricate the eyelid during blinking, both of which prevent dry eye and epitheliopathies.

Thus, to summarize, the meibomian glands 10 of mammalian (e.g., human) eyelids secrete oils that prevent evaporation of the tear film and provide lubrication to the eye and eyelids.

These meibomian glands 10 can become blocked or plugged (occluded) by various mechanisms leading to so-called "dry eye syndrome." While not the only cause, MGD is a known cause of dry eye syndrome. The disorder is characterized by a blockage of some sort within the meibomian glands 10 or at their surface, preventing normal lipid secretions from flowing from the meibomian glands 10 to form the lipid layer of the tear film. Such secretions serve to prevent evaporation of the aqueous tear film and lubricate the eye and eyelids 12, 14; hence, their absence can cause dry eye syndrome. Obstructions or occlusions 22, 24 of the meibomian glands 10 may be present over or at the orifice 16 of the meibomian gland 10, in the central duct 18 of the meibomian gland 10, which may be narrowed or blocked, or possibly in other locations including the passages from the acini 20 to the central duct 18.

In response to the foregoing, various treatment modalities have been developed in order to treat the dry eye condition, including drops, which are intended to replicate and replace the natural aqueous tear film and pharmaceuticals which are intended to stimulate the tear producing cells. For example, eye drops such as Refresh Endura™, Soothe™, and Systane™ brand eye drops are designed to closely replicate the naturally occurring healthy tear film. Other treatment modalities include various heating devices which are designed to assist in unclogging the meibomian glands by manual expression.

However, prior to implementing an appropriate treatment plan, the clinician must first determine whether some or all of the meibomian glands are properly secreting or are obstructed. If it is determined that the meibomian glands are obstructed, determining the degree of such obstruction is helpful in developing a treatment plan. The clinical evaluation of meibomian glands normally requires a test of their expressability. "Expressability" in this context is used to describe the ease with which secretion can be physically expelled from the meibomian gland.

MGD may be difficult to diagnose, because visible indicators are not always present. For example, meibomitis, an inflammation of the meibomian glands 10, can lead to MGD. Meibomitis may also be accompanied by blepharitis (inflammation of the eyelids). While meibomitis is obvious by inspection of the external eyelids, MGD may not be obvious even when examined with the magnification of a slit-lamp biomicroscope. This is because there may not be external signs or the external signs may be so minimal that they are overlooked. The external signs of MGD without obvious eyelid inflammation may be limited to subtle alterations of the orifices 16, overgrowth of epithelium over the orifices 16, and pouting of the orifices 16 of the meibomian glands 10 with congealed material acting as obstructions. In severe instances of MGD without obvious eyelid inflammation, the changes may be obvious, including serrated or undulated eyelid margins, orifice recession and more obvious overgrowth of epithelium over the orifices 16, and pouting of the orifices 16.

Current practice in diagnosing whether a meibomian gland is obstructed involves the application of force, usually with the thumb or finger to the external eyelid surfaces overlying the meibomian gland. The terms "gentle" and "forceful" expression have been used to describe the magnitude of the force used for meibomian gland evaluation. Further, as used herein, when referring to a "gland," the plural is intended to be included therein and when the term "glands" is used, the singular is intended to be included as well. Observations suggest that the diagnosis of whether an individual meibomian gland is obstructed is a function of the amount of force applied to the meibomian gland. While meibomian gland disease is often painful, clinicians often apply a force to the eyelid which is greater than the minimum force required to diagnose whether or not an obstruction exists, thus inflicting unnecessary pain on the patient.

SUMMARY OF THE DETAILED DESCRIPTION

Methods for diagnosing meibomian gland dysfunction are disclosed herein. It is important for a clinician to be able to determine whether the meibomian gland(s) are obstructed with normal and forced blinking since it is blinking that is the dynamic force that expresses the secretions of the meibomian gland(s) from the duct and through the orifice onto the eyelid margins and the tear film. It would be helpful to utilize a controlled method to simulate the forces of the eyelids in the act of blinking to mimic the action of the eyelids and the blink to express the secretions from the meibomian gland(s), thus allowing the diagnosis of obstruction of the meibomian gland(s). It is also desirable to provide a method of diagnosing meibomian gland obstruction or other dysfunction that is not painful, is inexpensive, and is easy to use. Preferably, the method would be standardized as much as possible to reduce the amount of variability dependent on who performs the diagnosis of the meibomian glands and to provide more accurate data gathering for the study of normal and abnormal meibomian gland function.

In one embodiment disclosed herein, a method of diagnosing meibomian gland dysfunction in an eye that can be standardized and that provides an accurate diagnosis of whether meibomian gland dysfunction exists is provided. The method utilizes an evaluation tool to apply a force for a preselected period of time to at least one of a plurality of meibomian glands in each of two or more regions of an eyelid. A grade is assigned to each meibomian gland of the plurality of meibomian glands in each of the plurality of regions based on any secretion that is expressed from each meibomian gland. In this manner, a plurality of meibomian gland secretion grades is obtained. The plurality of meibomian gland secretion grades is indicative of whether there is meibomian gland dysfunction.

In one embodiment, about five (5) meibomian glands in each of three (3) regions of the eyelid are evaluated and a grade is assigned to each of these meibomian glands such that grades are assigned to about fifteen (15) meibomian glands in the eye.

In one embodiment, the plurality of meibomian gland secretion grades is summed to get a total meibomian gland secretion score, wherein the total meibomian gland secretion score is indicative of whether there is meibomian gland dysfunction.

In another embodiment, the number of meibomian glands of the plurality of meibomian glands that yield a liquid secretion upon expression by the application of the force are summed to get a meibomian glands yielding liquid secretion (MGYLS) score that is indicative of whether or not meibomian gland dysfunction exists.

In another embodiment, the number of meibomian glands of the plurality of meibomian glands that yield a clear liquid secretion upon expression by the application of the force are summed to get a meibomian glands yielding clear secretion (MGYCS) score that is indicative of whether or not meibomian gland dysfunction exists.

In another embodiment, the plurality of meibomian gland secretion grades for one or more of the plurality of regions is summed to get one or more regional meibomian gland secretion scores, which may be indicative of whether there is meibomian gland dysfunction. In a further embodiment, one or more of the regional meibomian gland secretion scores are weighted to get a weighted meibomian gland secretion score, and the weighted meibomian gland secretion score is indicative of whether there is meibomian gland dysfunction.

The disclosed methods may be easy to use, minimize pain to the patient, and/or provide an accurate, objective, repeatable, and standardized test that allows for more accurate diagnosis and better treatment of meibomian gland dysfunction.

Those skilled in the art will appreciate the scope of the present invention and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the embodiments described herein, and together with the description serve to explain the principles of the embodiments described herein.

FIG. 6 is a table showing a meibomian gland secretion grading scale according to an exemplary embodiment;

DETAILED DESCRIPTION OF THE PREFERRED EMBODIMENTS

Figure 2:
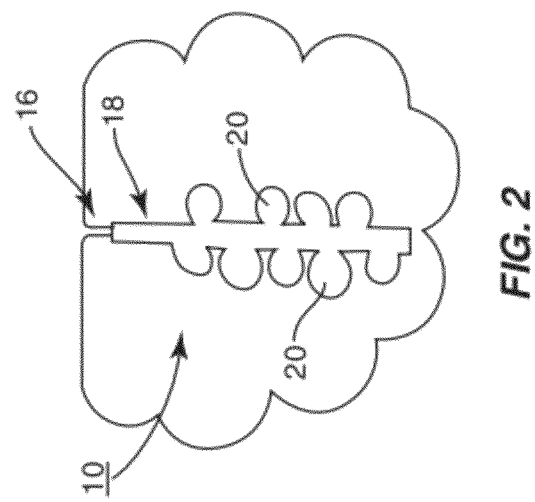
FIG. 2 illustrates an exemplary cutaway view of a meibomian gland.
Figure 1:
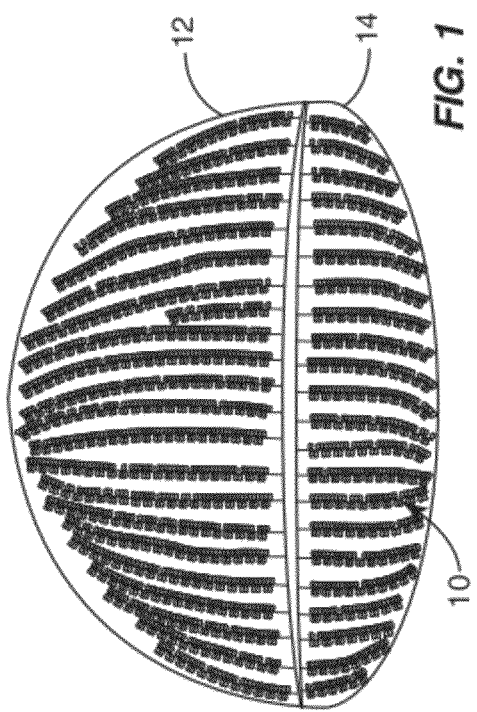
FIG. 1 illustrates exemplary upper and lower human eyelids showing the meibomian glands.

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

Methods for diagnosing meibomian gland dysfunction are disclosed herein. It is important for a clinician to be able to determine whether the meibomian gland(s) are obstructed with normal and forced blinking since it is blinking that is the dynamic force that expresses the secretions of the meibomian gland(s) from the duct and through the orifice onto the eyelid margins and the tear film. It would be helpful to utilize a controlled method to simulate the forces of the eyelids in the act of blinking to mimic the action of the eyelids and the blink to express the secretions from the meibomian gland(s), thus allowing the diagnosis of obstruction of the meibomian gland(s). It is also desirable to provide a method of diagnosing meibomian gland obstruction or other dysfunction that is not painful, is inexpensive, and is easy to use. Preferably, the method would be standardized as much as possible to reduce the amount of variability dependent on who performs the diagnosis of the meibomian glands and to provide more accurate data gathering for the study of normal and abnormal meibomian gland function.

In one embodiment, a method of diagnosing meibomian gland dysfunction in an eye that can be standardized and that provides an accurate diagnosis of whether meibomian gland dysfunction exists is provided. The method includes one or more clinical metrics based on the expressability of the meibomian glands. The method utilizes an evaluation tool to apply a force for a preselected period of time to at least one of a plurality of meibomian glands in each of two or more regions of an eyelid. A grade is assigned to each meibomian gland of the plurality of meibomian glands in each of the plurality of regions based on any secretion that is expressed from each meibomian gland. In this manner, a plurality of meibomian gland secretion grades is obtained. The plurality of meibomian gland secretion grades is indicative of whether there is meibomian gland dysfunction.

In one embodiment, about five (5) meibomian glands in each of three (3) regions of the eyelid are evaluated and a grade is assigned to each of these meibomian glands such that grades are assigned to about fifteen (15) meibomian glands in the eye.

In one embodiment, the plurality of meibomian gland secretion grades is summed to get a total meibomian gland secretion score, wherein the total meibomian gland secretion score is indicative of whether there is meibomian gland dysfunction.

In another embodiment, the number of meibomian glands of the plurality of meibomian glands that yield a liquid secretion upon expression by the application of the force are summed to get a meibomian glands yielding liquid secretion (MGYLS) score that is indicative of whether or not meibomian gland dysfunction exists.

In another embodiment, the number of meibomian glands of the plurality of meibomian glands that yield a clear liquid secretion upon expression by the application of the force are summed to get a meibomian glands yielding clear secretion (MGYCS) score that is indicative of whether or not meibomian gland dysfunction exists.

In another embodiment, the plurality of meibomian gland secretion grades for one or more of the plurality of regions is summed to get one or more regional meibomian gland secretion scores, which may be indicative of whether there is meibomian gland dysfunction. In a further embodiment, one or more of the regional meibomian gland secretion scores are weighted to get a weighted meibomian gland secretion score, and the weighted meibomian gland secretion score is indicative of whether there is meibomian gland dysfunction.

As discussed above, meibomian gland dysfunction or obstruction may compromise the adequacy of the tear film lipid layer. Meibomian gland obstruction due to multiple processes including epithelial overgrowth of the orifices and keratotic plugs of the ducts results in deficient or inadequate meibomian gland secretion. Meibomian gland obstruction frequently occurs without the obvious inflammatory and other characteristic external signs occurring with the frank forms of meibomitis and marginal and seborrheic blepharitis. Thus, it may be important for the clinician to determine whether the meibomian gland(s) are obstructed with normal and forced blinking since it is blinking that is the dynamic force that expresses the secretions of the meibomian gland(s) from the duct and through the orifice onto the eyelid margins and the tear film. The goal is to utilize a controlled method to simulate the forces of the eyelids in the act of blinking to mimic the action of the eyelids and the blink to express the secretions from the meibomian gland(s), thus allowing the diagnosis of obstruction of the meibomian gland(s). In addition, it may be beneficial to have an easy and repeatable process for assessing meibomian glands to determine whether meibomian gland dysfunction exists. In particular, an easy method that offers accuracy and repeatability by using one or more clinical metrics would be beneficial.

In this regard, methods are described herein for assessing meibomian gland dysfunction that include one or more clinical metrics based on the expressability of the meibomian glands to be used in the assessment. As an example, meibomian gland assessment may be performed at an initial baseline visit and at 2-week and 4-week follow-up visits. To evaluate the function of the meibomian glands, an ophthalmologist, technician, clinician, or other person (hereinafter "the evaluator") can assess the color and consistency of the secretion characteristics from the gland orifices along the lower eyelid. The evaluator can evaluate the glands, such as using a slit-lamp biomicroscope and a handheld diagnostic instrument as example, to apply gentle pressure along the eyelid margin, which simulates a forceful blink in yielding secretions from the meibomian glands. This method can provide a standardized method to apply the same amount of pressure at each visit and for each subject to ensure measurement consistency.

Figure 4:
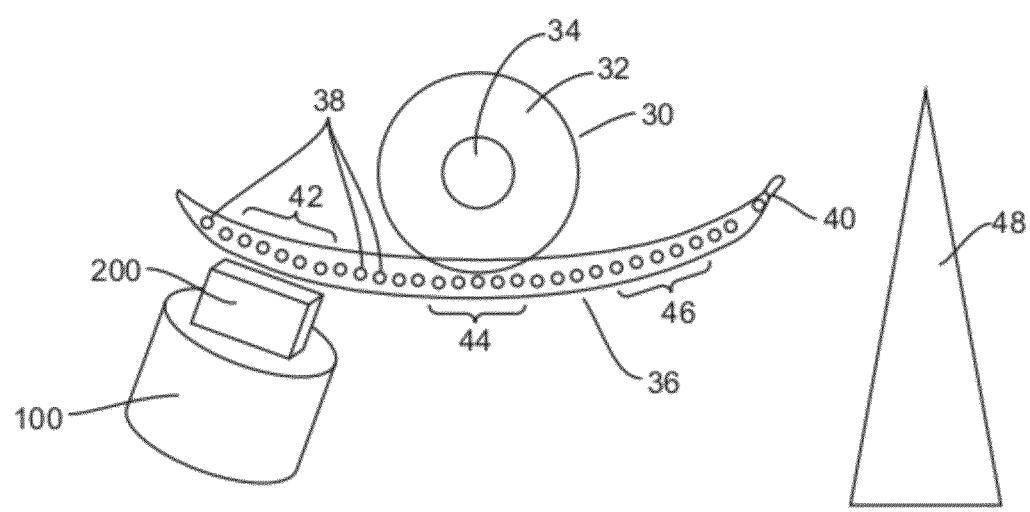
FIG. 4 illustrates the location of meibomian glands in the lower eyelid for assessment according to an exemplary embodiment.

FIG. 4 illustrates the location of meibomian glands in the lower eyelid for assessment according to an exemplary embodiment. Although FIG. 4 shows the meibomian glands in the lower eyelid, assessments may also be done for the meibomian glands in the upper eyelid. As seen in FIG. 4, the human eye has an eyeball 30 with an iris 32 and a pupil 34. A lower eyelid 36 contains a number of meibomian glands 38 and a lower punctum 40. On average, there are approximately twenty (20) to thirty (30) meibomian glands 38 along the lower eyelid 36. The lower eyelid 36 comprises a temporal region 42, a central region 44, and a nasal region 46. The nasal region 46 is the region of the lower eyelid 36 nearest a nose 48.

In one embodiment, at the baseline and follow-up visits, the evaluator assesses at least one of a plurality of meibomian glands in each of at least two (2) regions of an eyelid. In one embodiment, the evaluator may assess fifteen (15) meibomian glands located in three (3) regions of the eyelid 36, as shown in FIG. 4. In one embodiment, five (5) meibomian glands in each of the temporal, central, and nasal regions 42, 44, and 46 are assessed for a total of fifteen (15) meibomian glands. In one embodiment, the orifices of five (5) consecutive meibomian glands in each of the three (3) regions (the temporal region 42, the central region 44, and the nasal region 46) of the lower eyelid 36 may be identified and marked with nontoxic hypoallergenic face paint or a similar substance, anterior to the five (5) consecutive meibomian gland orifices. Although FIG. 4 shows the temporal, central, and nasal regions 42, 44, and 46 as comprising the five (5) meibomian glands 38 to be assessed in each region, each of the temporal, central, and nasal regions 42, 44, and 46 may comprise one or more meibomian glands 38 in both directions and thus may comprise more or less than five (5) meibomian glands 38.

The center of a meibomian gland evaluation tool 100 or other instrument should be carefully placed in the temporal, central and nasal regions 42, 44, and 46 as described in the procedure below to avoid overlap in the meibomian gland assessment. The meibomian gland evaluation tool 100 may be any apparatus used by the evaluator to test meibomian glands. Examples of the meibomian gland evaluation tool 100 are disclosed more fully below in FIGS. 8A-15 and the accompanying description. In general, the meibomian gland evaluation tool 100 may include a handle (not shown in FIG. 4) and a probe tip 200 mounted for movement relative to the handle such that when the probe tip 200 is placed against an eyelid (such as the lower eyelid 36 in FIG. 4) and a force is applied, the force required for natural expression of secretion from the meibomian gland is replicated.

Figure 5:
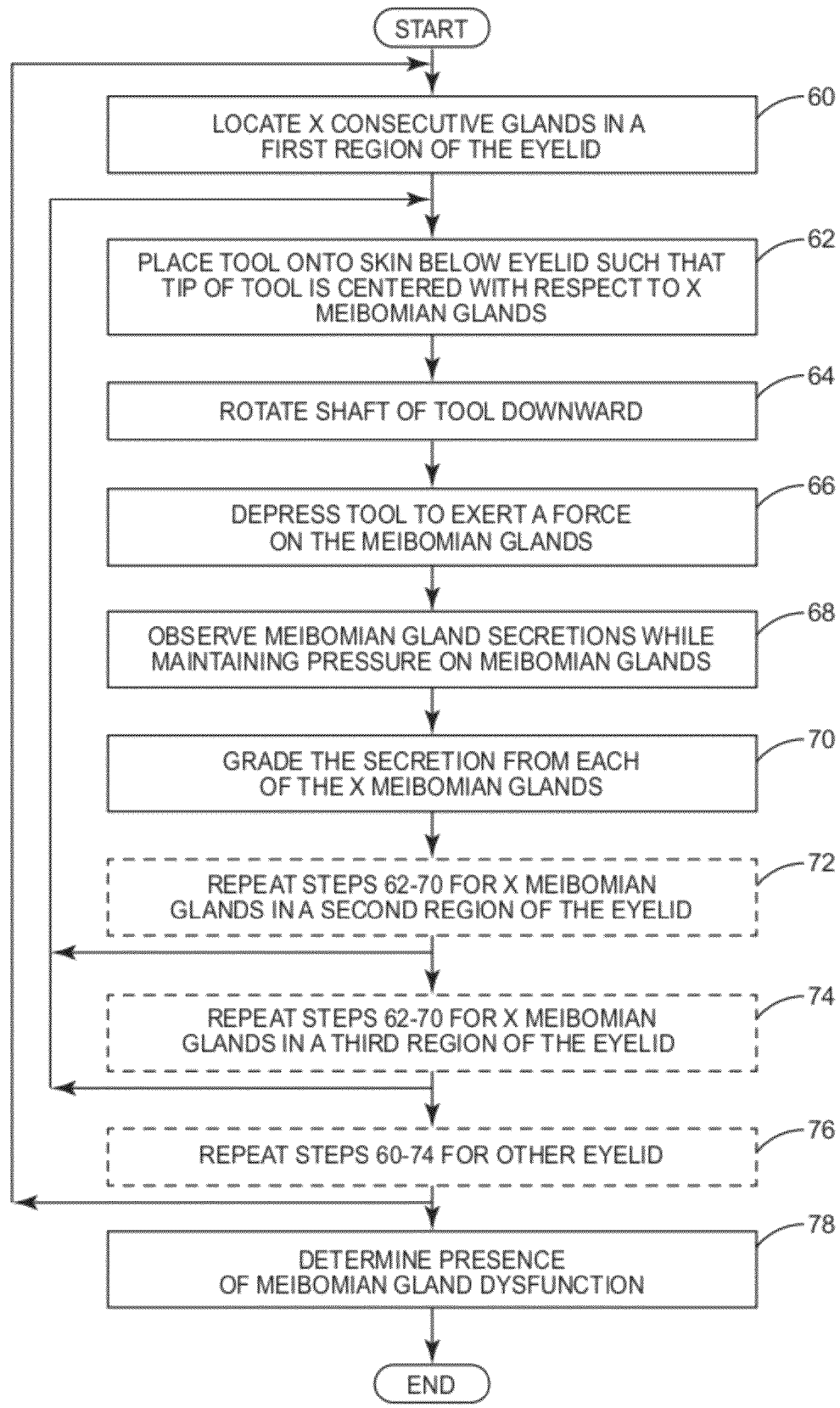
FIG. 5 is a flowchart illustrating a method of assessing meibomian glands according to an exemplary embodiment.

Referring to FIG. 4 and the flowchart in FIG. 5, a method of assessing meibomian glands according to an exemplary embodiment is described. The following procedure is one non-limiting embodiment of the method used for examination and grading of meibomian gland function.

Under a slit-lamp biomicroscope (not shown), in step 60 of FIG. 5, the evaluator locates a first region (which in the embodiment shown in FIG. 4 may be the temporal region 42 of the lower eyelid 36) and observes a number x (where x is at least one (1)) of meibomian glands 38. In one embodiment, five (5) consecutive meibomian glands 38 may be observed in the temporal region 42. Note that the orifices of the meibomian glands 38 are what are mostly observed. In one embodiment, the slit-lamp biomicroscope may have 10× to 16× magnification.

In step 62, the evaluator places a contact surface of the meibomian gland evaluation tool 100 having the probe tip 200 onto the skin immediately below a lash line of the lower eyelid 36 so that the long dimension is parallel to the eyelid margin, and a number x of meibomian glands 38 (where x is at least one (1)) are centered with respect to the probe tip 200 of the meibomian gland evaluation tool 100. In one embodiment, the probe tip 200 is centered over five (5) meibomian glands 38. The evaluator may hold the meibomian gland evaluation tool 100 between the forefinger and the thumb.

In step 64, once full contact is achieved between the contact surface of the meibomian gland evaluation tool 100 and the outer skin of the lower eyelid 36, the evaluator rotates the shaft of the instrument downward approximately fifteen (15) to forty-five (45) degrees so that it is tangential to the eyeball 30.

In step 66, the evaluator then depresses the meibomian gland evaluation tool 100 to exert a force on the meibomian glands 38 that are being assessed. In one embodiment, the force exerted is a standard constant force. The standard constant force may be exerted normal to the eyeball 30 in one embodiment. The standard constant force in one embodiment simulates the pressure exerted by a forceful blink of the eyelid upon a meibomian gland. Testing has determined that this force is approximately fifteen (15) grams per thirty (30) mm² (or 0.5 g/mm²). However, depending upon age, gender, race or other factors, this force may be between ten (10) grams per thirty (30) mm² and twenty (20) grams per thirty (30) mm² or even up to forty (40) to sixty (60) grams per thirty (30) mm² in some cases. The evaluator should be cognizant of the amount of force applied as an amount of force that is much greater than the pressure exerted by a forceful blink of the eyelid upon a meibomian gland may express material from a meibomian gland that is not healthy and functioning. Thus, using too much force may result in expressing secretory material that is not useful, and potentially disadvantageous, in making a diagnosis of meibomian gland dysfunction. For an accurate diagnosis, it is preferable to evaluate the initial secretory material that is expressed with the optimum amount of force.

The evaluator may adjust the position of the meibomian gland evaluation tool 100 to cause the flat surface of the eyelid margin of the lower eyelid 36 to roll slightly outward, facilitating a clear view of the orifices of the meibomian glands 38. The exertion of the force on the meibomian glands 38 should result in the expression of secretion from the meibomian glands 38 if the meibomian glands 38 are functional.

In step 68, to facilitate observation of the meibomian gland secretions, the evaluator may gently wipe clean the orifices of the meibomian glands 38 along the eyelid margin of the lower eyelid 36 with a dry cotton swab immediately after applying pressure while maintaining the meibomian gland evaluation tool 100 in position and maintaining pressure.

Figure 3:
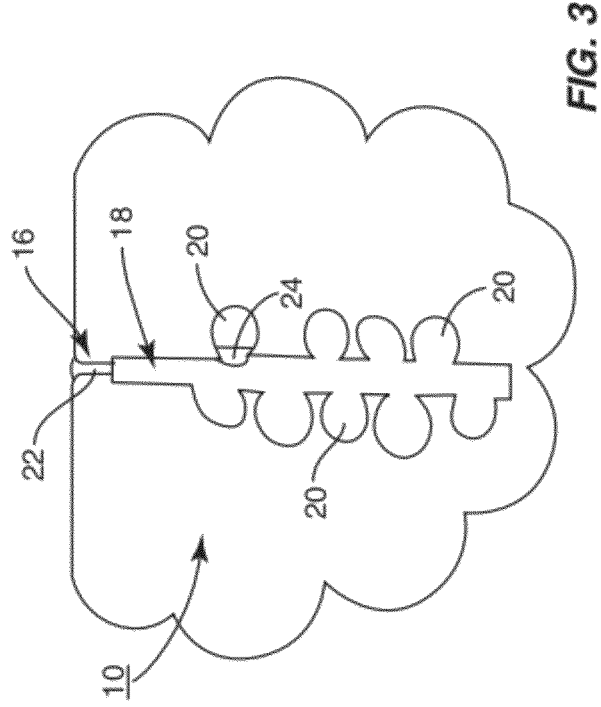
FIG. 3 illustrates an exemplary cutaway view of a meibomian gland having several clogging mechanisms.

In step 70, the evaluator may grade the secretion from each of the meibomian glands 38 by holding the meibomian gland evaluation tool 100 in place over the meibomian glands 38 for a minimum of ten (10) and a maximum of fifteen (15) seconds while evaluating the secretion characteristics from each meibomian gland 38. In one embodiment, in lieu of, or in addition to, holding the meibomian gland evaluation tool 100 in place over the meibomian glands 38 for a minimum time period, the evaluator may hold the meibomian gland evaluation tool 100 in place over the meibomian glands 38 until a certain volume of secretions are expressed from the meibomian glands 38. In order to accurately evaluate the meibomian glands 38, the meibomian gland evaluation tool 100 may be used to standardize the force exerted on the meibomian glands 38. In one embodiment, no additional force should be applied after the shaft of the meibomian gland evaluation tool 100 has been depressed approximately three (3) millimeters. Applying additional force may negate the benefit of using an instrument that applies a standard force. In one embodiment, the expressed secretion from each meibomian gland 38 is assigned a grade according to the characteristics shown in the table of FIG. 6. For each of the plurality of meibomian glands that are assessed (which is fifteen (15) meibomian glands in the embodiment of FIG. 4), the evaluator grades the expressed secretion characteristics on a scale of 0-3, as shown in the table of FIG. 6. A grade of 3 may be assigned for clear liquid secretion; a grade of 2 may be assigned for cloudy liquid secretion; a grade of 1 may be assigned for an inspissated/ toothpaste consistency; and a grade of 0 may be assigned for no secretion. Other grading scales may also be used. For example, the grade may also depend on the relative quantity of any secretion that is observed. In addition, if a standard force (such as the amount of force of a forceful blinking of the eyelid) is placed on the outer eyelid, and an instantaneous release of secretory material is observed, a high grade may be given to that meibomian gland because such an instantaneous release of secretory material may be indicative of a healthy meibomian gland. However, the ten (10) to fifteen (15) seconds time period is sometimes required to express secretory material from a distal portion of the meibomian gland well below the surface of the orifice of the meibomian gland (see FIG. 3).

In optional step 72 (as indicated by the dashed box), the evaluator may then move the meibomian gland evaluation tool 100 over to a second region of the lower eyelid 36 (which may be the nasal region 46 of the lower eyelid 36 in one embodiment) and observe at least one of a plurality of meibomian glands 38 in the second region. In one embodiment, the evaluator may observe five (5) consecutive glands 38 in the nasal region 46. Steps 62-70 above may then be repeated for the evaluation of the secretion characteristics for the at least one meibomian gland of the plurality of meibomian glands that is observed in the second region (which may be five (5) meibomian glands 38 in the nasal region 46 in one embodiment). In one embodiment, this will result in the assignment of grades to five (5) meibomian glands 38 in the nasal region 46.

In optional step 74 (as indicated by the dashed box), the evaluator may then move the meibomian gland evaluation tool 100 over to a third region of the lower eyelid 36 (which may be the central region 44 of the lower eyelid 36 (directly below the pupil 34) in one embodiment) and observe at least one of a plurality of meibomian glands 38 in the third region. In one embodiment, the evaluator may observe five (5) consecutive meibomian glands 38 in the central region 44. The evaluator may then repeat the evaluation of the secretion characteristics in steps 62-70 above for the at least one meibomian gland of the plurality of meibomian glands that is observed in the third region (which may be five (5) meibomian glands 38 in the central region 44). In one embodiment, this will result in the assignment of grades to five (5) meibomian glands 38 in the central region 44.

It should be noted that the evaluation of meibomian glands in the third region may be beneficial but is not necessarily required to obtain a score sufficient to make a determination of meibomian gland dysfunction. The evaluation and grading of at least one meibomian gland of the plurality of meibomian glands in any two (2) of the three (3) regions of the eyelid may be sufficient to determine the presence of meibomian gland dysfunction. Further, which two (2) regions are evaluated is not critical.

In step 76, the evaluator may then repeat steps 60-74 above to evaluate the secretion characteristics for an eyelid of the other eye, although this step is optional. For example, the other eye may be evaluated only if it is necessary to make a determination of meibomian gland dysfunction in the other eye.

Note that although in the above steps the meibomian glands 38 in the temporal region 42 were assessed first, followed by the nasal region 46, and then the central region 44, the regions may be assessed in any order.

Figure 7:
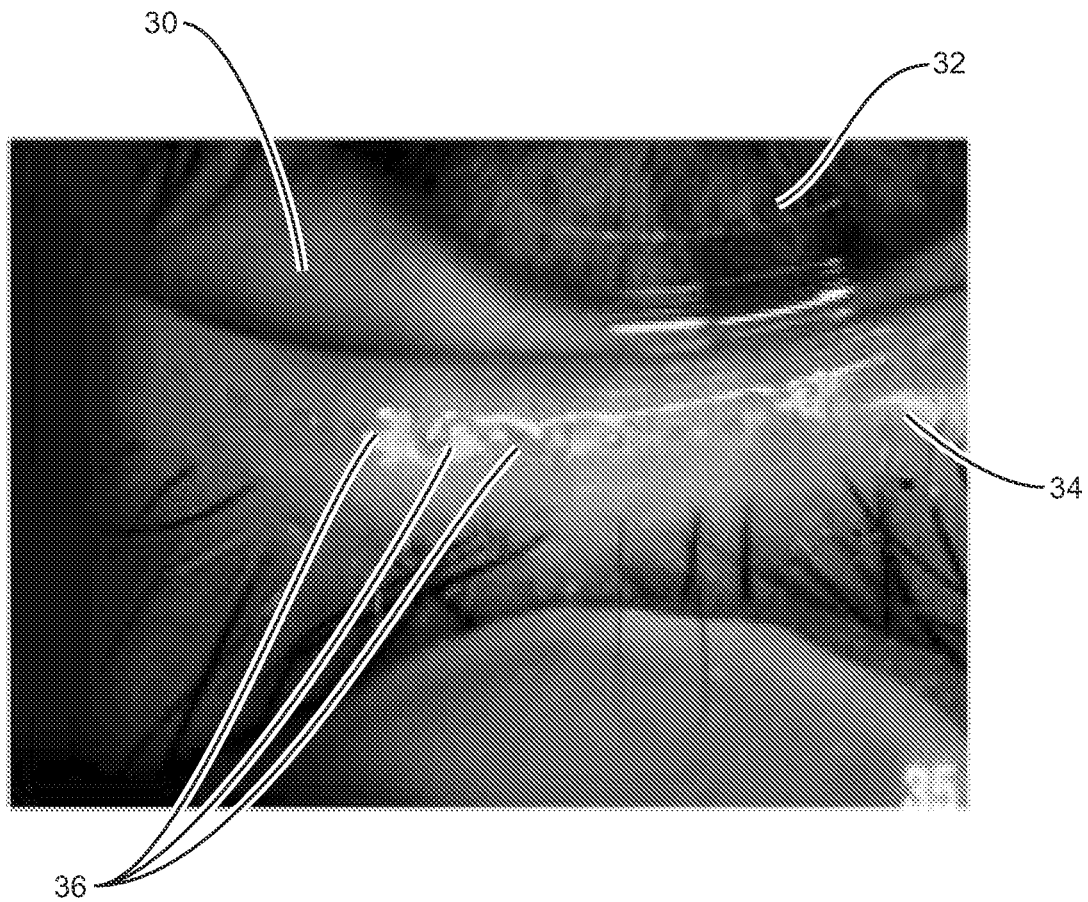
FIG. 7 is a color picture illustrating an example of a meibomian gland yielding clear liquid at a meibomian gland orifice.

In step 78, a determination is made as to the presence of meibomian gland dysfunction. The determination is made based on the data collected as part of the evaluation of the meibomian glands 38. Various metrics and data analysis involving the grades assigned to the assessed meibomian glands 38 may be used as part of the determination of the presence of meibomian gland dysfunction. For data analysis, as one non-limiting example, the total meibomian gland secretion score for each eye may be calculated based on the sum of the secretion grades for all of the meibomian glands 38 that were evaluated on the lower eyelid 36. In one embodiment, as shown in FIG. 4, the total meibomian gland secretion score is the sum of the grades assigned to all fifteen (15)

meibomian glands that were graded. Alternatively, a regional meibomian gland secretion score may be obtained for each region 42, 44, 46 of the lower eyelid 36 by adding the secretion grades for the particular region. In addition, the number of meibomian glands 38 yielding clear liquid secretion (i.e., having a secretion score of 3, an example of which is shown in FIG. 7) may be calculated. Further, the number of meibomian glands 38 yielding any liquid secretion (a grade of 2 or 3 in the table of FIG. 6) may be calculated.

Thus, for data analysis, several metrics may be calculated from the meibomian gland assessment to assist in determining whether meibomian gland dysfunction exists and how severe the meibomian gland dysfunction may be. The first metric may be a total meibomian gland secretion score. In the total meibomian gland score, the scores for all of the evaluated meibomian glands 38 in the lower eyelid 36 (which is fifteen (15) meibomian glands in one embodiment) may be summed to calculate the total meibomian gland secretion score. In the embodiment where fifteen (15) meibomian glands are graded, the total meibomian gland score can range from zero (0) to forty-five (45), with forty-five (45) being the maximum possible total meibomian gland secretion score for the fifteen (15) meibmian glands (three (3) being the highest possible grade for each meibomian gland). The total meibomian gland score may be indicative of whether meibomian gland dysfunction exists. A higher score indicates less meibomian gland dysfunction, while the lower the score, the higher the degree of meibomian gland dysfunction. In one embodiment, a baseline total meibomian gland secretion score of 12 or less (on a scale of 0 to 45) is considered to be evidence of meibomian gland dysfunction that should be treated.

The total meibomian gland secretion score that is obtained by observing and grading five (5) meibomian glands in each of the three (3) regions of the eyelid for a total of fifteen (15) meibomian glands has been found to be a particularly effective and accurate indicator of the presence of meibomian gland dysfunction. However, other metrics, as discussed below, may also be effective and accurate in determining meibomian gland dysfunction.

Another metric that may be used in determining meibomian gland dysfunction is the number of meibomian glands 38 yielding clear liquid secretion (the meibomian glands 38 that were graded a 3) of the fifteen (15) meibomian glands 38 that were assessed. The number of meibomian glands 38 yielding clear liquid secretion may be referred to as the Meibomian Glands Yielding Clear Secretion (MGYCS) score. Clear liquid secretion is the optimal secretion quality. The MGYCS score may be indicative of whether meibomian gland dysfunction exists. A higher number of meibomian glands 38 yielding clear secretion indicates less meibomian gland dysfunction. In one embodiment, if four (4) or less of the fifteen (15) assessed meibomian glands 38 were assessed to have yielded clear liquid secretion (a grade of 3), this may result in a diagnosis of meibomian gland dysfunction that should be treated. If nine (9) or more of the fifteen (15) assessed meibomian glands 38 were assessed to have yielded clear liquid secretion (a grade of 3), then there is a low probability of dry eye due to meibomian gland dysfunction.

The number of meibomian glands that yield clear secretions has been found to be highly indicative and correlative to whether meibomian gland dysfunction exists, with a higher number of meibomian glands 38 yielding clear secretion indicating less meibomian gland dysfunction and a lower number of meibomian glands 38 yielding clear secretion indicating that meibomian gland dysfunction may be present.

Another metric that may be used in determining meibomian gland dysfunction is the number of meibomian glands 38 that secrete any liquid. This includes any meibomian glands 38 that were graded as a 2 or 3 (clear or cloudy liquid) of the fifteen (15) meibomian glands 38 that were assessed. The number of meibomian glands 38 yielding any sort of liquid secretion may be referred to as the Meibomian Glands Yielding Liquid Secretion (MGYLS) score. The MGYLS score may be indicative of whether meibomian gland dysfunction exists. The higher the number of meibomian glands 38 that secrete any liquid is indicative of less meibomian gland dysfunction; thus, a lower MGYLS score may indicate that meibomian gland dysfunction requiring treatment exists.

A further metric is to consider the number of meibomian glands 38 in each of the regions 42, 44, 46 of the eyelid that secrete any liquid (a grade of 2 or 3) or that secrete clear liquid (a grade of 3). A regional meibomian gland secretion score may be obtained for each region 42, 44, 46 of the lower eyelid 36 by adding or summing the secretion grades for the particular region. The regional meibomian gland secretion scores may be indicative of whether meibomian gland dysfunction exists. The regional meibomian gland secretion scores may also be weighted to get a weighted meibomian gland secretion score. For example, the meibomian glands 38 in the temporal region 42 of the lower eyelid 36 do not typically secrete as much on average as the meibomian glands 38 in the central region 44 or the nasal region 46. Thus, more weight may be given to the meibomian gland secretion scores for the meibomian glands 38 in the central region 44 or the nasal region 46. The meibomian glands 38 in the nasal region 46 tend to secrete the most of the three (3) regions on average, so the meibomian glands 38 in the nasal region 46 may be weighted the most in one embodiment.

Any of the metrics disclosed above can be calculated for the whole lower eyelid 36, or for each of the temporal, central, and nasal regions 42, 44, and 46 of the lower eyelid 36. In addition, though FIG. 4 shows assessing the meibomian glands in the lower eyelid 36, the same procedure could be done for the upper eyelid. In this manner, the methods disclosed above may be employed with the upper eyelid to obtain a total meibomian gland secretion score, or the number of meibomian glands that secrete any liquid, or the number of meibomian glands yielding clear liquid secretion, in either the whole upper eyelid, or in the various regions of the upper eyelid.

As discussed above, a meibomian gland evaluation tool may be used to test the meibomian glands. In particular, the meibomian gland evaluation tool 100 in one embodiment exerts a force that simulates the force required for natural expression of secretion from the meibomian gland by the forceful blinking of an eyelid. In one embodiment, this force is a standard constant force. In a further embodiment, the force may be approximately fifteen (15) grams per thirty (30) $mm^2$. However, depending upon age, gender, race or other factors, this force may be between ten (10) grams per thirty (30) $mm^2$ and twenty (20) grams per thirty (30) $mm^2$ or even up to forty (40) grams per thirty (30) $mm^2$ in some cases. FIGS. 8A-15 below describe several exemplary embodiments of the meibomian gland evaluation tool 100 that may be used to carry out the methods described above.

Figure 8A:
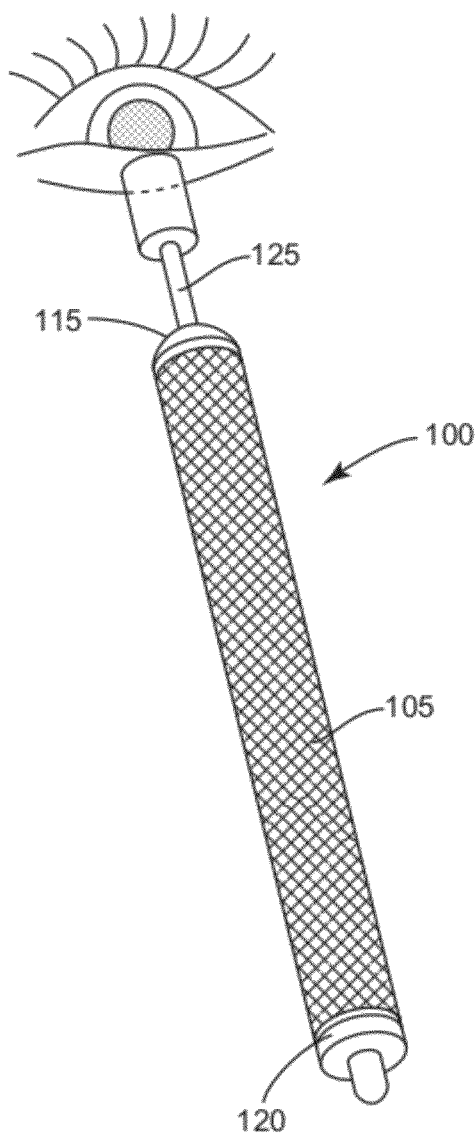
FIG. 8A is a perspective view of an exemplary embodiment of a meibomian gland evaluation tool showing a small tip for evaluation of one or just a few meibomian glands.
Figure 8B:
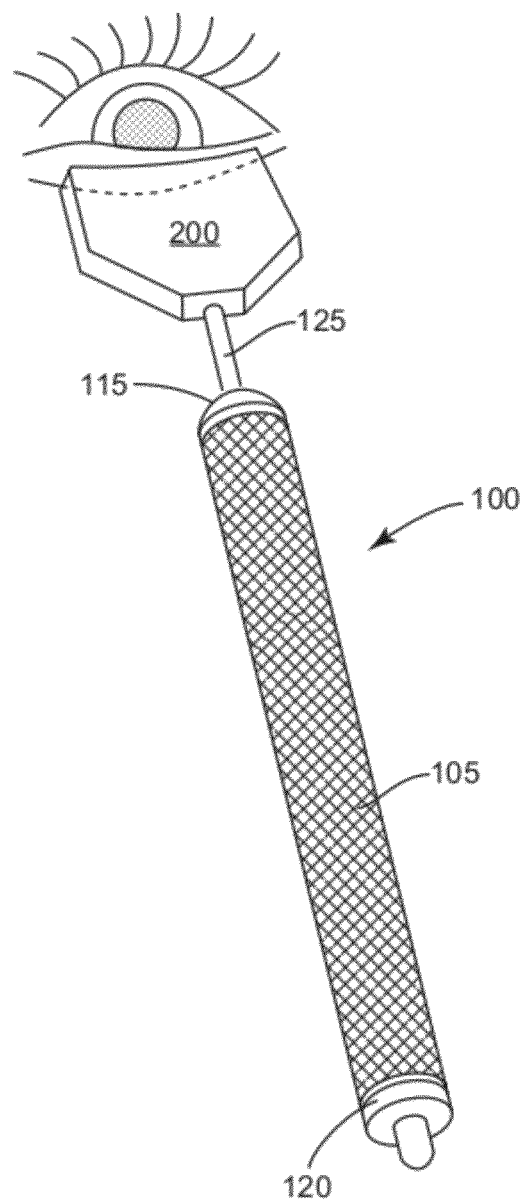
FIG. 8B is a perspective view of an exemplary embodiment of the meibomian gland evaluation tool of FIG. 8A showing a larger tip for evaluation of several meibomian glands.
Figure 9:
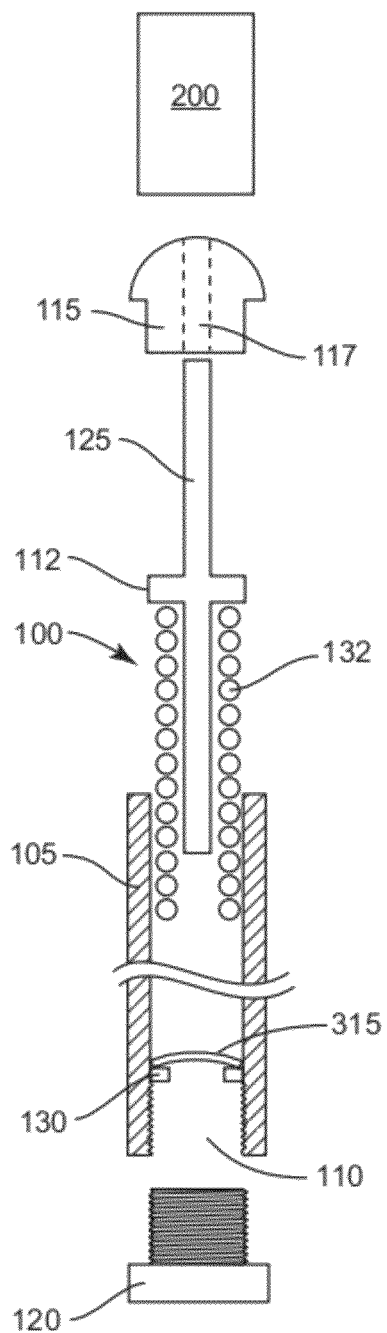
FIG. 9 is a broken-away side view of an exemplary embodiment of the meibomian gland evaluation tool of FIGS. 8A and 8B.

Referring to the figures and particularly FIGS. 8A, 8B, and 9, a meibomian gland evaluation apparatus (also referred to as a meibomian gland evaluation tool) 100 is shown. The meibomian gland evaluation tool 100 allows for the application of a standard constant force during the expression portion of a meibmoian gland assessment, which provides for a more repeatable and standardized assessment and diagnosis procedure, as well as more accurate data. The ability to more easily and accurately collect data on the expressibility of meibomian glands allows an evaluator or diagnostician to better be able to diagnose meibomian gland dysfunction, such as by using an evaluation tool like the meibomian gland evaluation tool 100 described above to assess a plurality of meibomian glands in each of a plurality of regions of an eyelid. This allows an evaluator to collect data on a large number of meibomian glands in the eyelid. A grade may be assigned to each meibomian gland of the plurality of meibomian glands in each of the plurality of regions based on any secretion that is expressed from each meibomian gland. In this manner, a plurality of meibomian gland secretion grades is obtained, which provides a better and more accurate indication of whether there is meibomian gland dysfunction.

In this embodiment, the meibomian gland evaluation tool 100 comprises an elongated shaft or handle 105 having a bore 110 therethrough. Located at one end of the handle 105 is an annulus 112, the purpose of which will become evident as the description proceeds. One end of the handle 105 mounts an end cap 115 having a bore 117 therethrough and the opposite end of the handle 105 mounts a second end cap 120. The end caps 115, 120 may be threaded, press-fitted, or otherwise connected, depending upon the particular fabrication technique and materials employed. For purposes of illustration only, the end cap 115 is press-fitted and the second end cap 120 is threaded. It will be noted that in most instances the meibomian gland evaluation apparatus 100 will be used in conjunction with a slit-lamp biomicroscope and that the handle 105 should be of an appropriate dimension to be used in conjunction therewith.

A probe tip 200 is mounted for longitudinal movement relative to the handle 105 such that when the probe tip 200 is placed against the eyelid and compressive force is applied, moving the handle 105 a preselected distance replicates the approximate force required for natural expression of secretion from the meibomian gland. Testing has determined that this force is approximately fifteen (15) grams per thirty (30) mm$^2$. However, depending upon the age, gender, race or other factors, this force may be between ten (10) grams per thirty (30) mm$^2$ and twenty (20) grams per thirty (30) mm$^2$ or even up to forty (40) grams per thirty (30) mm$^2$ in some cases. The probe tip 200 is detachably connected to one end of a shaft 125 which is operatively associated with the handle 105. The probe tip 200 may be fabricated from a soft biocompatible material such as natural or synthetic rubber, Polyester™, or other inert/non-allergenic or biocompatible materials, well known to those skilled in the art.

Figure 10:
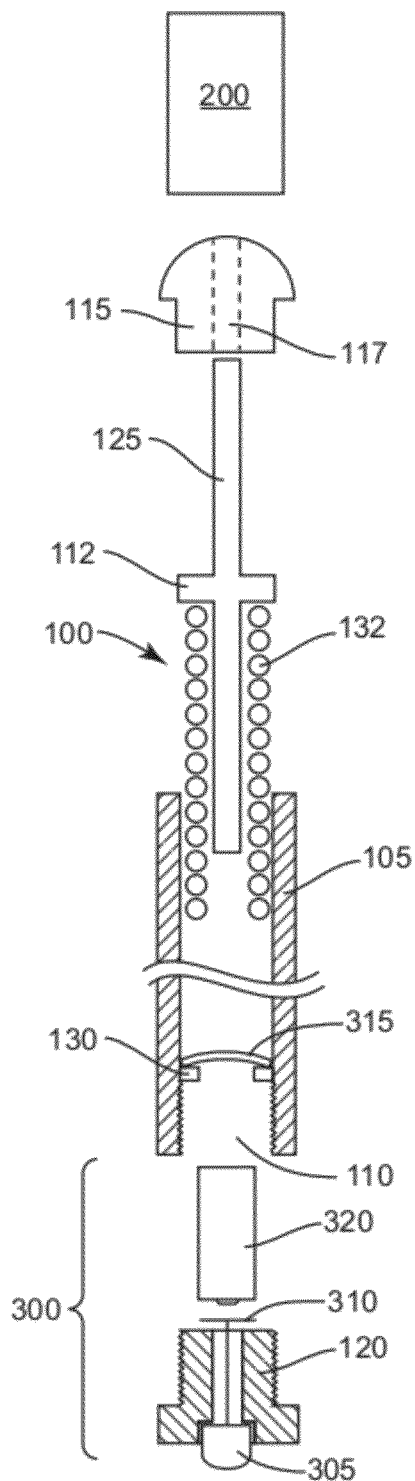
FIG. 10 is a perspective view of another exemplary embodiment of the meibomian gland evaluation tool of FIGS. 8A and 8B.
Figure 11:
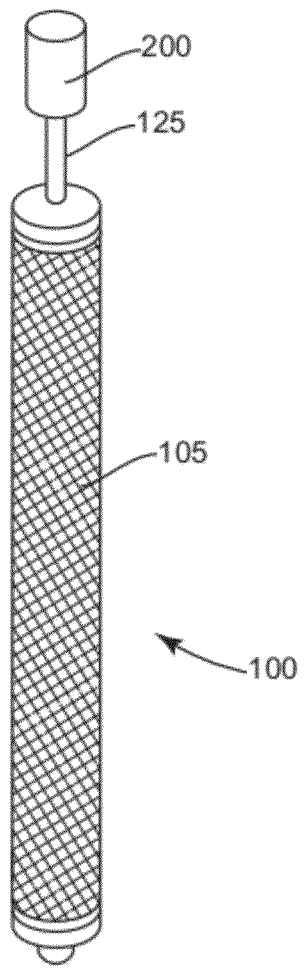
FIG. 11 is a broken away side view of another exemplary embodiment of the meibomian gland evaluation tool of FIGS. 8A and 8B.

As shown in FIGS. 8A and 11, the probe tip 200 may be cylindrical and may be dimensioned to overlie one or more meibomian glands. An alternate embodiment of the probe tip 200 is shown connected to the handle as illustrated in FIGS. 8A, 9, and 10, and in that embodiment the probe tip 200 is designed to test a larger section (approximately ¼) of the eyelid to simultaneously evaluate multiple meibomian glands for gland function. In one embodiment, as shown in FIG. 8B, the probe tip 200 may be paddle-shaped. In one embodiment, the probe tip 200 is dimensioned such that the surface of the probe tip 200 that makes contact with the eyelid is configured to apply pressure to the eyelid evenly. In a further embodiment, the probe tip 200 may be capable of applying pressure evenly over a portion of the eyelid that contains at least five or more meibomian glands. The probe tip 200 may be press fit, snapped or threaded onto the end of the handle 105. In addition, in one embodiment, the probe tip 200 may be thirty (30) mm$^2$ in size. However, it is to be understood that this size is exemplary of probe tips and that larger or smaller surface areas may be employed with equal efficacy, depending on the preference of the clinician, the equipment employed, the degree of obstruction present, as well as other factors which may appear. Thus, the pressure per unit area to be tested will remain substantially unchanged. For example, a probe tip of fifteen (15) mm$^2$ will have a pressure ranging between five (5) grams per fifteen (15) mm$^2$ and ten (10) grams per fifteen (15) mm$^2$ according to the parameters set out above. Stated otherwise, under normal circumstances the probe tip will apply a pressure between ⅓ and ⅔ grams per mm$^2$.

Per FIG. 9, the handle 105 may also include the annulus 112 proximate the tip mounting end. As shown, the shaft 125 is inserted within the bore 110 for longitudinal movement. A helical spring 132 is operatively associated with the handle 105 and surrounds a section thereof, biasing the handle 105 out of the housing. An annulus 130 serves as a support or bearing surface for the helical spring 132.

As illustrated in a second embodiment, shown in FIG. 10, the meibomian gland evaluation apparatus 100 may also include an indicator means or indicator 300 for indicating when the handle 105 has moved the preselected distance. The indicator means 300 may be selected from the group consisting of auditory, visual, and tactile signals. Any of the aforementioned signal means may be employed so long as activation thereof does not significantly impact the force required to move the handle to ensure that the pressure delivered to the eyelid remains in the required range. The indicator means 300 comprises a visual indicator means or light emitting diode (LED) 305 mounted in the second end cap 120 such that the light emitting portion is at least partially external of the second end cap 120 and electrical leads 310 (schematically shown) extend down into the bore 110 and are connected to a battery contact plate 315 also within the handle 105. A battery 320 is provided proximate the battery contact plate 315. The LED 305 is activated by movement of the handle 105 which causes the end of the shaft 125 to complete the electrical circuit and illuminate the LED 305. Movement of the handle 105 away from the eyelid opens the electrical circuit and turns off the LED 305. Circuits of this nature are well known the art and a detailed discussion thereof is not deemed necessary. Buzzers, vibrators or other indicator means may also be employed as visual indicator means.

Figure 12:
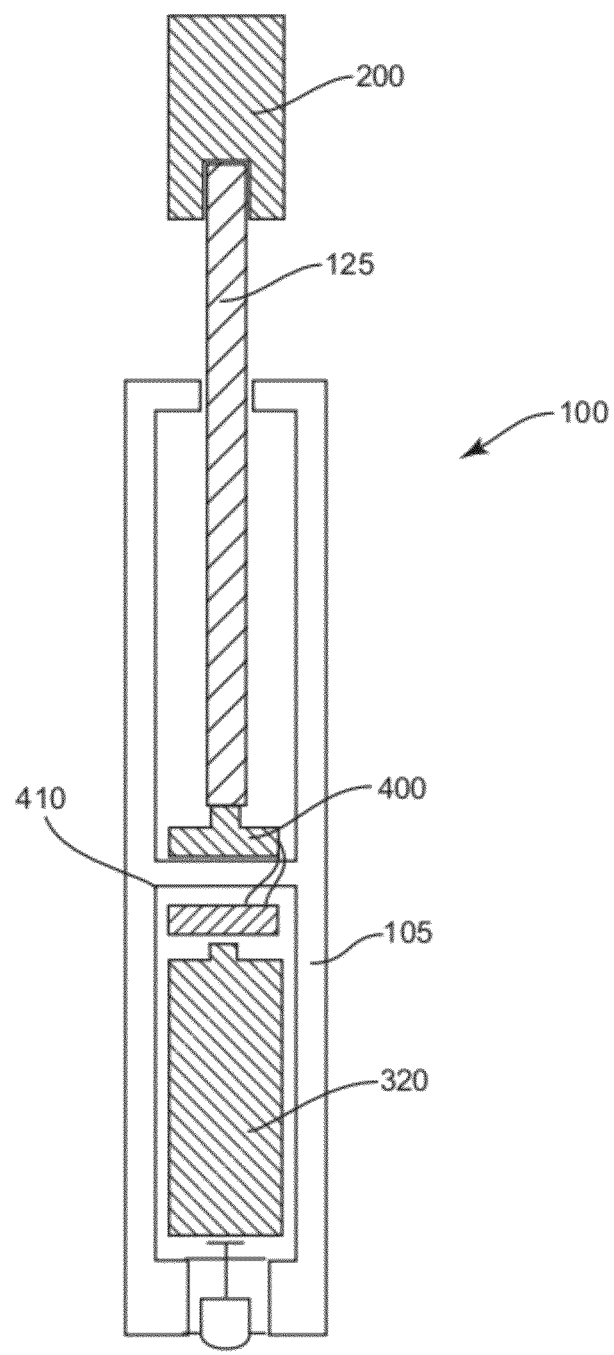
FIG. 12 is a broken away side view of another exemplary embodiment of the meibomian gland evaluation tool of FIGS. 8A and 8B.

In the embodiment of FIG. 12, the meibomian gland evaluation tool 100 is generally similar to the previously described embodiment except that the shaft 125 is substantially stationary, and the means for sensing when the preselected pressure has been reached comprises a piezo-electric or other similar strain gauge device 400 in combination with an amplification circuit 410 (shown schematically) and which is well known to those skilled in the art. When the preselected pressure has been exerted on the eyelid, the amplification circuit 410 is activated and the indicator means 300 is triggered. It is believed that this embodiment may be produced using molding techniques wherein the cylindrical handle 105 will be produced in two (2) longitudinal halves and will be press fit together.

Figure 13:
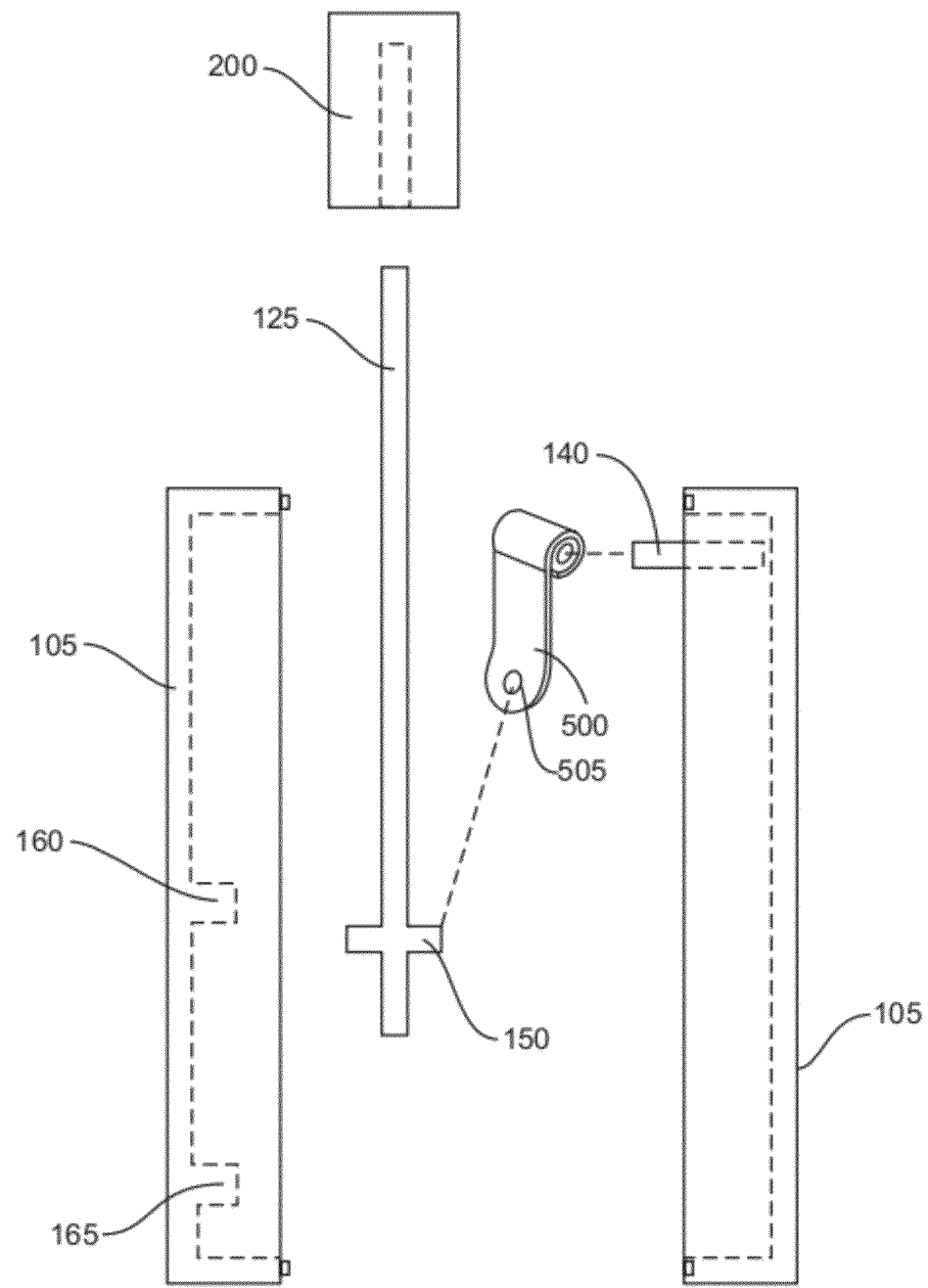
FIG. 13 is an exploded side view of another exemplary embodiment of the meibomian gland evaluation tool of FIGS. 8A and 8B.

In the embodiment of FIG. 13, the preselected pressure is supplied by a spring means or constant force spring 500 which has a spring constant selected to deliver the preselected pressure to the eyelid. The constant force spring 500 is coiled and has a connection opening 505 at the outer end. In this embodiment, it is again believed that the handle 105 will be molded in two (2) opposing longitudinal sections that will be press fit together. One half of the handle 105 is provided with an upper stop 160 and a lower stop 165 in the form of protuberances extending into the bore 110 which operate to limit the travel of the shaft 125, as will be described more fully herein below. In addition, one side of the handle includes a tang 140 extending from the inner handle wall towards the center of the bore 110. The tang 140 should be of a diameter to receive the opening in the center of the constant force spring 500 and should be of a length sufficient to maintain the constant force spring 500 in place when the two halves of the handle 105 are connected together. The other end of the constant force spring 500 is connected to a tang 150 located on the shaft 125. In the "at rest" state of this embodiment, the constant force spring 500 is in the coiled position and the tang 150 is in contact with the upper stop 160. Pressure exerted on the probe tip 200 by movement of the handle 105 causes the constant force spring 500 to uncoil until the tang 150 contacts the lower stop 165. An indicator means is not provided as the constant force is delivered merely by unwinding the constant force spring 500. Further, it is believed that the clinician will sense when the shaft 125 has reached its maximum path of travel when the tang 150 contacts the lower stop 165, but the indicator means 300, which could buzz, flash, vibrate, or illuminate when the shaft 125 is in the operating range between the stops 160 and 165 previously described, could also be included with this embodiment.

Figure 14:
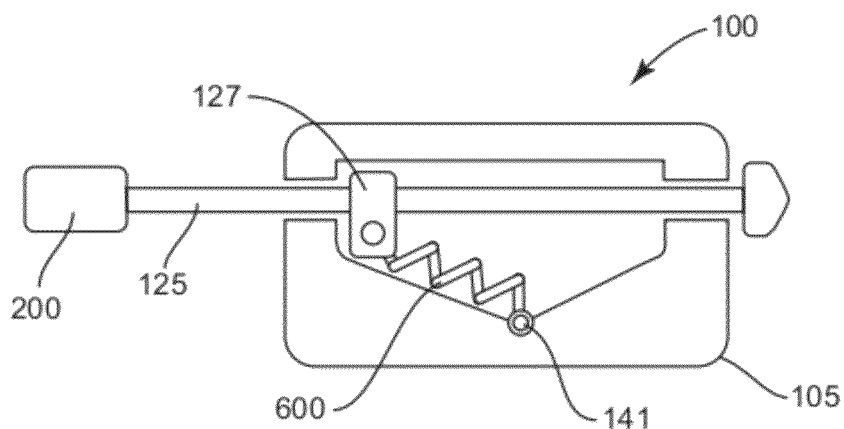
FIG. 14 is a broken-away side view of another exemplary embodiment of the meibomian gland evaluation tool of FIGS. 8A and 8B.

FIG. 14 illustrates an alternate embodiment of the meibomian gland tool 100 wherein the handle shape is rectangular and box-like. The shaft 125 includes a mounting bracket 127 to which one end of an over center spring or compression spring 600 is connected. As the compression spring 600 is normally expanded, a first end rests in a cavity or pocket 141 in the handle 105. The opposite end of the compression spring 600 is connected to the handle 105 by means of a pin or tang formed in the housing of the handle 105 and the shaft 125 is biased in the extended or outward position. Pressure on the eyelid acts to compress the compression spring 600. When the handle 105 is pushed past the cavity or pocket 141, the handle 105 will retract away from the eyelid. The device may be reset by pressing a reset button (not shown), which is well known to those skilled in the art.

Figure 15:
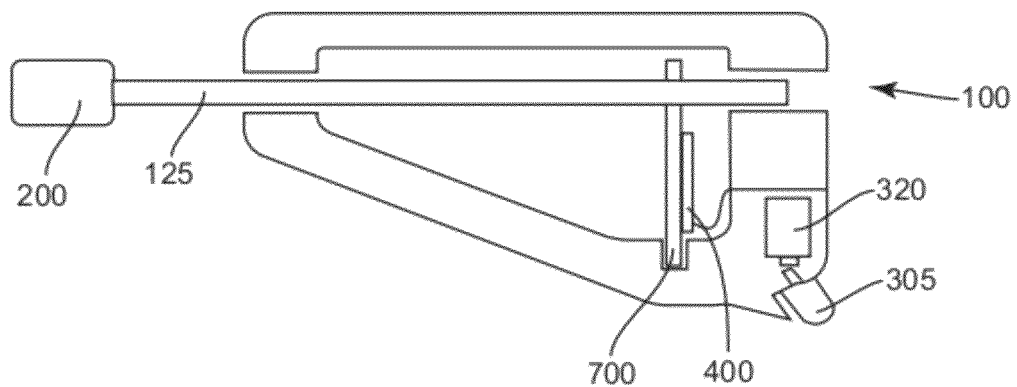
FIG. 15 is broken-away side view of another exemplary embodiment of the meibomian gland evaluation tool of FIGS. 8A and 8B.

FIG. 15 illustrates another embodiment of the meibomian gland evaluation tool 100 wherein the shaft 125 is connected to the handle 105 with a cantilever beam 700. A piezo-electric transducer or strain gauge device 400 is included, together with actuator circuitry identical to that discussed in connection with the embodiment of FIG. 12. Pressure on the probe tip 200 causes the strain gauge device 400 to output a signal proportional to the applied pressure. When the preselected pressure has been reached, the actuator circuit activates the LED 305.

In operation, the clinician selects the handle 105 having the desired probe tip 200 or mounts the desired probe tip 200 at the end of the shaft 125. The probe tip 200 is then placed on the external surface of that section of the eyelid to be tested for meibomian gland function. The clinician also equips himself with the proper equipment (appropriate magnification from a hand held lens, head magnifier, slit-lamp biomicroscope, microscope, etc.) to be able to observe the meibomian gland orifice(s) in order to monitor whether secretion is expressed from the orifices of the meibomian gland with the application and the continuation of a compressive force. The compressive force in the form of gentle pressure is exerted upon the eyelid by pressing the handle 105 towards the eyelid, which compresses the helical spring 132. In one embodiment, just prior to the end of the shaft 125 making contact with the battery contact plate 315, the force of fifteen (15) grams per thirty (30) $mm^2$ is reached in a user independent manner and the clinician observes whether the meibomian gland is properly secreting or not, and the type of abnormality of secretion varying from total obstruction to compromised secretion. The meibomian gland evaluation tool 100 may be designed so that just prior to activation of the indicator means 300, the cumulative force or energy stored in the helical spring 132 is substantially equivalent to the force required for natural meibomian gland secretion. Of course, other indicator means are actuated in the aforementioned manner as well.

In another embodiment (not shown) of the meibomian gland evaluation tool 100, the shaft 125 may be connected to the handle 105 which is attached to a coil spring of constant force. The coil spring of constant force rotates and provides force either directly on the eyelid or by pushing a linear rod attached to the handle 105, which applies force on the eyelid.

It will be noted that in one embodiment, the meibomian gland evaluation tool 100 may be fabricated as a disposable, single use item primarily from plastic materials, or alternatively, may be fabricated as a multiple use probe with disposable tips, in which case that portion of the device that is re-used will be fabricated from materials of sufficient durability to withstand repeated autoclaving and/or alcohol sterilization, as appropriate for the materials chosen.

Although the meibomian gland evaluation tool 100 described above is particularly well-suited for collecting the expressibility data, other tools may also be used.

Therefore, it is to be understood that the invention is not to be limited to the specific embodiments disclosed and that modifications and other embodiments are intended to be included within the scope of the appended claims. It is intended that the present invention cover the modifications and variations of this invention provided they come within the scope of the appended claims and their equivalents. Although specific terms are employed herein, they are used in a generic and descriptive sense only and not for purposes of limitation.

What is claimed is:

1. A method of diagnosing meibomian gland dysfunction in an eye, comprising:
   placing an evaluation tool on an outer portion of an eyelid;
   applying a force to at least one of a plurality of meibomian glands in each of at least two regions of a plurality of regions of the eyelid for a preselected period of time using the evaluation tool, wherein the force applied by the evaluation tool is a standard constant force that simulates forceful blinking of the eyelid;
   assigning a grade to the at least one of the plurality of meibomian glands in each of the at least two regions of the plurality of regions based on any secretion that is expressed from each meibomian gland to obtain a plurality of meibomian gland secretion grades indicative of a presence of meibomian gland dysfunction; and
   summing the plurality of meibomian gland secretion grades to obtain a total meibomian gland secretion score, wherein the total meibomian gland secretion score is indicative of the presence of meibomian gland dysfunction.

2. The method of claim 1, further comprising applying the force to four to six meibomian glands in each of three regions of the eyelid and a grade is assigned to each of these meibomian glands.

3. A method of diagnosing meibomian gland dysfunction in an eye, comprising:
   placing an evaluation tool on an outer portion of an eyelid;
   applying a force to at least one of a plurality of meibomian glands in each of at least two regions of a plurality of regions of the eyelid for a preselected period of time using the evaluation tool, wherein the force applied by the evaluation tool is a standard constant force that simulates forceful blinking of the eyelid; and assigning a grade to the at least one of the plurality of meibomian glands in each of the at least two regions of the plurality of regions based on any secretion that is expressed from each meibomian gland to obtain a plurality of meibomian gland secretion grades indicative of a presence of meibomian gland dysfunction, wherein the grade assigned to each of the meibomian glands is a first grade for clear liquid secretion; a second grade for cloudy liquid secretion; a third grade for a secretion having an inspissated/toothpaste consistency; and a fourth grade for no secretion.

4. The method of claim 3, further comprising summing the plurality of meibomian gland secretion grades to obtain a total meibomian gland secretion score.

5. The method of claim 4, wherein the first grade is a three (3), the second grade is a two (2), the third grade is a one (1), and the fourth grade is a zero (0), and a total meibomian gland secretion score of 12 or less is indicative of the presence of meibomian gland dysfunction.

6. The method of claim 3, further comprising summing the number of meibomian glands of the plurality of meibomian glands having a first grade or a second grade to get a meibomian glands yielding liquid secretion (MGYLS) score that is indicative of the presence of meibomian gland dysfunction.

7. The method of claim 3, further comprising summing the number of meibomian glands of the plurality of meibomian glands having a first grade to get a meibomian glands yielding clear secretion (MGYCS) score that is indicative of the presence of meibomian gland dysfunction.

8. The method of claim 7, wherein a MGYCS score of 4 or less is indicative of the presence of meibomian gland dysfunction.

9. The method of claim 7, wherein a MGYCS score of 9 or greater is indicative that meibomian gland dysfunction is unlikely.

10. The method of claim 1, wherein the standard constant force is between ten (10) grams per thirty (30) $mm^2$ and forty (40) grams per thirty (30) $mm^2$.

11. The method of claim 1, wherein the preselected period of time is between approximately ten (10) and fifteen (15) seconds.

12. The method of claim 1, wherein the plurality of regions comprises a temporal region, a central region, and a nasal region.

13. The method of claim 1, further comprising summing the plurality of meibomian gland secretion grades for at least one region of the plurality of regions to get a regional meibomian gland secretion score, wherein the regional meibomian gland secretion score is indicative of whether there is meibomian gland dysfunction.

14. The method of claim 1, wherein applying the force further comprises placing the evaluation tool on an outer portion of the eyelid, rotating a shaft of the evaluation tool downward, and depressing the evaluation tool approximately three (3) millimeters (mm).

15. The method of claim 1, wherein the plurality of meibomian gland secretion grades indicates that meibomian gland dysfunction is likely.

16. The method of claim 15, further comprising treating the meibomian gland dysfunction.

17. The method of claim 16, wherein the treating the meibomian gland dysfunction varies based on the plurality of meibomian gland secretion grades.

18. A method of diagnosing meibomian gland dysfunction in an eye, comprising:
    placing an evaluation tool on an outer portion of an eyelid;
    applying a force to at least one of a plurality of meibomian glands in each of at least two regions of a plurality of regions of the eyelid for a preselected period of time using the evaluation tool, wherein the force applied by the evaluation tool is a standard constant force that simulates forceful blinking of the eyelid; and
    assigning a grade to the at least one of the plurality of meibomian glands in each of the at least two regions of the plurality of regions based on any secretion that is expressed from each meibomian gland to obtain a plurality of meibomian gland secretion grades indicative of a presence of meibomian gland dysfunction; and
    summing the plurality of meibomian gland secretion grades for each of the plurality of regions to get a plurality of regional meibomian gland secretion scores, wherein one or more of the regional meibomian gland secretion scores are weighted more heavily to get a weighted meibomian gland secretion score and the weighted meibomian gland secretion score is indicative of whether there is meibomian gland dysfunction.

19. The method of claim 18, wherein more weight is given to the regional meibomian gland secretion scores for the meibomian glands in the central region and the nasal region.

20. The method of claim 18, wherein more weight is given to the regional meibomian gland secretion scores for the meibomian glands in the nasal region.

* * * * *